United States Patent [19]

Neyra et al.

[11] Patent Number: 5,697,186
[45] Date of Patent: Dec. 16, 1997

[54] FLOCCULATED MICROBIAL INOCULANTS FOR DELIVERY OF AGRICULTURALLY BENEFICIAL MICROORGANISMS

[75] Inventors: Carlos A. Neyra, Kendall Park; Alahari Arunakumari, Highland Park; Olubayi Olubayi, New Brunswick, all of N.J.

[73] Assignee: Rutgers, The State University Of New Jersey, Piscataway, N.J.

[21] Appl. No.: 454,317

[22] PCT Filed: Feb. 24, 1994

[86] PCT No.: PCT/US94/01997

§ 371 Date: Jun. 5, 1995

§ 102(e) Date: Jun. 5, 1995

[87] PCT Pub. No.: WO94/19924

PCT Pub. Date: Sep. 15, 1994

[51] Int. Cl.$^6$ .................. A01C 1/06; C12N 1/04; C05F 11/08
[52] U.S. Cl. .................. 47/57.6; 47/58; 71/6; 71/7; 424/93.3; 424/93.47; 424/93.48; 435/252.1; 435/252.2; 435/252.4; 435/253.3
[58] Field of Search .................. 47/56.7, 58; 71/6, 71/7; 435/252.1, 252.2, 253.3, 252.4; 424/93.3, 93.47, 93.48

[56] References Cited

U.S. PATENT DOCUMENTS 4,583,320  4/1986  Redenbaugh .................. 47/57.6

OTHER PUBLICATIONS

Bleakley et al. Floc formation by *Azospirillum lipoferum* grown on poly–B–hydroxybutyrate. Applied Environmental Microbiology vol. 54, pp. 2986–2995 1988.

Okon. *Azospirillum* as a potential inoculant for agiriculture. Trends in Biotechnology. vol. 3, pp. 223–228 1985.

Bashan, J., Applied and Environmental Microbiology 51:1089–1098, 1986.

Deinema, M. et al., Arch. Mikrobiol. 78:42–57, 1971.

Fages, J., in *Azospirillum/Plant Associations*, Yaacov Okon, ed. CRC Press 1994, ch.6.

Lamm, R.B., et al., Can. J. Micro. 27:1320–1325, 1981.

Mugnier, J., et al., Appl. and Environ. Micro 50:108–114, 1985.

Napoli, C., et al., Appl. and Environ. Micro. 30:123–131, 1975.

Okon, Y., et al., *Microbial Inoculants as Crop–Yield Enhancers*, in CRC Critical Reviews in Biotechnology, Boca Raton, FL, CRC Press, 1987 pp. 61–85.

Sadasivan, L., et al., J. Bact. 163:716–723, 1985.

Stormo, K., et al., Appl. and Environ. Micro. 58:727–730, 1992.

*Primary Examiner*—Douglas W. Robinson
*Assistant Examiner*—Melissa L. Kimball
*Attorney, Agent, or Firm*—Dann, Dorfman, Herrell and Skillman, P.C.

[57] ABSTRACT

Flocculated bacterial cells are utilized as high-density crop inoculants and delivery systems for one or more agriculturally beneficial microorganisms. The flocculated form of bacteria, such as Azospirillum and Rhizobium, possess superior survivability under storage, as a seed coating and mixed seed priming media. Other microorganisms may be co-flocculated with the aforementioned bacteria, thereby providing a crop inoculant for delivery of multiple agriculturally beneficial microorganisms.

16 Claims, No Drawings

FLOCCULATED MICROBIAL INOCULANTS FOR DELIVERY OF AGRICULTURALLY BENEFICIAL MICROORGANISMS

FIELD OF THE INVENTION

This invention relates to the use of microorganisms to enhance crop productivity and, more specifically, to the use of flocculated forms of bacteria, particularly Azospirillum, Rhizobium, or a combination thereof, as crop inoculants and delivery systems for other agriculturally beneficial microorganisms.

BACKGROUND OF THE INVENTION

Many microorganisms are known to exert beneficial effects on plant growth. Among these are the well-known nitrogen-fixing Rhizobium species, which are symbionts of leguminous species. Azospirillum species, which are free-living nitrogen-fixing bacteria associated with the roots of grasses, are also now recognized for their plant growth-promoting qualities.

It has been shown that Azospirillum can be induced to transform from vegetative cells to desiccation-resistant encysting forms under limiting cultural conditions (i.e., culture media providing the minimal amount of nutrients required for growth). This transformation is accompanied by the overproduction of exocellular polymers that cause aggregation and extensive flocculation of the cells in culture. Sadasivan et al., J. Bact., 163:716–23 (1985).

Rhizobium species have also been observed to flocculate in culture medium and in association with roots. Napoli et al., App. Microbiol., 30:123–31 (1975); Deinema et al., Arch. Mikrobiol., 78:42–57 (1971). Unlike Azospirillum, flocculation dynamics of Rhizobium heretofore have not been studied. No distinctions have been made between microscopic aggregates and the massive aggregation of cells characteristic of Azospirillum cultured under specified conditions (e.g., suitable carbon source, low nitrogen content and high C:N ratio).

Inoculation of seeds or soil with beneficial microorganisms for crop improvement has been practiced for a number of years. However, variable and inconsistent results have often been obtained due to loss of inoculant viability or variability of dosage due to changes in inoculant viability. Okon et al., CRC Crit. Rev. Biotechnology, 6:61–85 (1987).

One of the most commonly used carriers for commercial inoculants of agriculturally beneficial microorganisms is peat. For Rhibozium and Azospirillum species, bacteria are cultured in fermentors to reach high population levels (i.e., $\sim 10^9$ cells/ml), then added to pre-sterilized peat. The inoculum thereafter may be applied to seeds (by preparing a slurry containing the peat/bacteria mixture and gums or sugars to improve adhesion), by applying directly to soil (e.g., by dripping peat suspensions into planting furrows) or by mixing with other planting media. Okon et al., supra. Each of these delivery methods suffers from inconsistent dosage due to loss of viability under varied seed storage or field condition. Okon et al., supra.

Several other formulations of crop inoculants have been proposed in an attempt to overcome problems with loss of viability and inconsistent dosage. These methods involve entrapment of living cells in various biopolymers, such as polyacrylamide (Dommergues et al., Appl. Environ. Microbiol., 37:779–81, 1979), xanthan and carob gums (Mugnier et al., Appl. Environ. Microbiol., 50:108–114, 1985) and alginate (Bashan, Appl. Environ. Microbiol., 51:1089–98, 1986; Fages, Appl. Microbiol. Biotechnol., 32:473–78, 1990).

Although entrapment of microorganisms in biopolymers increases the concentration and stability of inoculants, the production of such inoculants often involves multiple steps and requires specialized equipment. For example, one method of preparing alginate beads carrying Azospirillum involves the following steps: (1) growing Azospirillum in nutrient broth; (2) adding sodium alginate, along with various other ingredients, to the culture broth containing the Azospirillum cells; (3) extruding the mixture under pressure through 1 mm plastic nozzles, the resulting drops being projected into a 6 g/l $CaCl_2$ solution to form alginate beads containing entrapped bacteria; (4) removing the $CaCl_2$ solution; and (5) dehydrating the beads by air-drying, freeze-drying or oven-drying. Fages, Appl. Microbiol. Biotechnol., 32:473–78 (1990). Such methods are time-consuming and can be expensive. Moreover, bacteria entrapped in alginate beads may not adhere well to seeds, and therefore, may not be optimally suitable for coating seeds with inoculant. The agricultural industry would clearly benefit from a simple, less expensive method of providing microbial inoculants for plants, seeds and soil.

SUMMARY OF THE INVENTION

In accordance with the present invention, a simple, rapid method is provided for producing a crop inoculant for delivery of agriculturally beneficial microorganisms. The method utilizes the biological property of certain bacteria, such as Azospirillum, Rhizobium and Zooglia, among others, wherein, under pre-determined culture conditions, bacterial cells differentiate into an encysted form and aggregate together to produce a flocculent form. Flocculation under these conditions is so extensive that the flocculent sinks to the bottom of a culture medium container, and is readily separable from the medium.

According to one aspect of the present invention, a method is provided for delivering a microorganism to a plant, for purposes of improving plant productivity. The plant is inoculated with a microbial inoculant comprising a flocculated form of the microorganism, preferably Azospirillum or Rhizobium, or a combination thereof. Plants may be inoculated in a variety of ways, including coating seeds of the plant with the inoculant, mixing the inoculant into planting and germination mixtures or seed priming media, or applying the inoculant to aboveground portions of plants.

According to another aspect of the present invention, there is provided a microbial inoculant for a plant, which comprises a flocculated form of bacterium, preferably Azospirillum or Rhizobium, or a combination thereof. In a preferred embodiment, the inoculant further comprises at least one other microorganism. The microbial inoculant is prepared by culturing the bacterium and, optionally, the other microorganism(s) in a flocculation growth medium, then transferring log-phase cells to a medium comprising mineral salts and organic acids necessary for microbial growth, a carbon source and a nitrogen source, the ratio of carbon to nitrogen in the medium being at least 30:1 and preferably about 80:1. The culture is placed under conditions promoting the growth of each microorganism and flocculation of the bacterium, thereby forming a co-floc comprising the flocculated bacterium and the other microorganism(s). The co-floc is then harvested to produce a microbial inoculant comprising the flocculated bacterium, which may also comprise at least one other microorganism.

In a preferred embodiment of the present invention, a co-floc comprising both Azospirillum and Rhizobium is prepared as a microbial inoculant for a plant. Because both Azospirillum and Rhizobium flocculate extensively in the flocculation medium, a co-floc comprising both bacteria in flocculated form is easily produced. This microbial inoculant is prepared by culturing Azospirillum species and Rhizobium species in a growth medium, then transferring log-phase cells to a flocculation medium comprising mineral salts and organic acids necessary for microbial growth, a carbon source and a nitrogen source, the ratio of carbon to nitrogen in the medium being at least 30:1 and preferably about 80:1. The culture is placed under conditions promoting the growth and flocculation of both bacteria, thereby forming a co-floc, which is then harvested to produce a microbial inoculant comprising both bacteria in a flocculated form.

The above-described microbial inoculant is used to inoculate seeds. According to another aspect of the present invention, a coated seed is provided in which the seed coating comprises a flocculated form of bacterium, preferably Azospirillum and/or Rhizobium and, optionally, at least one other microorganism.

According to another aspect of the invention, a planting mixture is provided which comprises a planting medium and a microbial inoculant comprising a flocculated form of bacterium, preferably Azospirillum and/or Rhizobium and, optionally, at least one other microorganism.

According to a further aspect of the invention, a seed priming medium is provided which comprises a solid matrix and a microbial inoculant comprising a flocculated form of bacterium, preferably Azospirillum and/or Rhizobium and, optionally, at least one other microorganism.

The use of flocculated bacteria as an inoculant and delivery system for other microorganisms provides many advantages over current systems for providing inoculant. Flocculated bacterial cells, such as Azospirillum and Rhizobium, are produced in standard batch cultures or fermentors, using media that induces cell differentiation and aggregation. These bacterial aggregates, i.e., flocs, form large clumps that separate easily from culture fluid upon standing for a few minutes. Therefore, separation of the inoculant does not require special centrifugation procedures.

Inoculum produced by flocculating bacteria possesses a long shelf life. Flocs can be stored moist, under refrigeration, or can be air-dried and stored for long period of time. Seeds and flocs can be mixed and stored for several months. Flocculated bacteria possess enhanced survivability on dry surfaces such as seeds and soil, due to the presence of many bacterial cells in encysted form, which confers desiccation resistance and prolongs cell viability. Flocculated bacterial cells exude an extensive polysaccharide network, which also contributes to the enhanced survivability and shelf life of the flocs. Additionally, the polysaccharide matrix enhances adhesiveness of the inoculant to solid surfaces, such as seeds. Therefore, there is no need to pre-treat seeds with an adhesive before applying the inoculant.

Another significant advantage of using flocculated bacteria is that other plant growth-promoting microorganisms can be co-flocculated with the flocculating bacteria to produce an inoculant containing multiple agriculturally beneficial microorganisms. The polysaccharide network of bacterial flocs confers a certain amount of stability on these other co-flocculated microorganisms as well.

DETAILED DESCRIPTION OF THE INVENTION

The following words and phrases are defined for reference in the specification as follows:

1. Flocculation: The process of cell differentiation and aggregation undergone by certain microorganisms in response to environmental or chemical stimuli, involving the production of a massive biopolymer network to form macroscopic cell aggregates. Cells may be induced to flocculate by altering the nutrient culture conditions under which cells are grown, or by the addition of various chemical agents, according to methods commonly known in the art.

2. Floc, Flocculent: The fluffy mass formed by the aggregation of microbial cells undergoing flocculation. In the present invention, bacterial flocs are macroscopic aggregates that settle to the bottom of a liquid culture upon standing. This type of macroscopic flocculation is also observable as a reduction in optical density of a liquid culture, due to settling of the bacterial flocs. The term "flocculent" is also sometimes used herein as a noun, interchangeably with the term "floc". The term "flocculent" is also used as an adjective to describe the growth pattern of cells in the process of flocculation, i.e., a "flocculent" growth or growth pattern.

3. Co-floc, Co-flocculation: The product of (or process of) co-culturing two flocculating microorganisms, such as Azospirillum and Rhizobium, or of co-cultivating one or more flocculating microorganisms with one or more additional non-flocculating microorganisms. This involves inoculating the bacterial culture with the additional microorganisms prior to flocculation, such that the additional microorganisms are entrapped in the biopolymer network produced by the flocculating bacteria.

4. Mixed floc: The product of combining already-flocculated bacteria with at least one additional microorganism. Mixed flocs are different from co-flocs in that the additional microorganisms are mixed with flocculated bacteria after flocculation, instead of prior to flocculation, as in co-flocs.

5. Microbial inoculant, inoculum: An inoculant or inoculum composed of one or more microorganisms, at least one of which is a flocculating microorganism, such as Azospirillum and/or Rhizobium. These microbial inoculants are utilized in the present invention for delivering beneficial microorganisms to plants.

6. Plant productivity, crop productivity: Refers generally to any aspect of growth or development of a plant that is a reason for which the plant is grown. For example, when referring to food crops, such as grains or vegetables, crop productivity generally refers to the yield of grain or fruit, etc., harvested from a particular crop. However, for "crops" such as turf grass, plant productivity may refer to growth rate, turf density, disease resistance or the like. Thus, for purposes of the present invention, improved plant or crop productivity refers broadly to improvements in yield of grain, fruit, flowers, or other plant parts harvested for various purposes, improvements in growth of plant parts, including stems, leaves and roots, improved resistance to disease, improved survivability in extreme climate, and similar improvements to the growth and development of plants.

The phenomenon of flocculation has been extensively studied as a model system to understand cell-cell interaction in aggregated forms. Flocculation is of major interest in the brewing industry, as flocculated yeast are utilized extensively as inoculants. However, use of flocculated cells for agricultural purposes is novel, and its use in delivery of plant beneficial microorganisms should substantially enhance crop productivity.

In accordance with the present invention, a flocculated bacterium, such as Azospirillum and/or Rhizobium, is utilized as a high-density crop inoculum and delivery system for one or more agriculturally beneficial microorganisms. Flocculated microorganisms possess superior stability and adhesive characteristics, as compared with crop inoculants heretofore available.

Any microorganism that can be induced to flocculate can be utilized in the practice of the present invention. The most useful microorganisms are those such as Azospirillum or Rhizobium, which can be induced to flocculate simply by growing them in a nutrient-limited culture medium.

In accordance with the present invention, it has also been determined that *Zooglia spp.* can be induced to flocculate under the same culture conditions as *Azospirillum* or *Rhizobium*. Thus, although any flocculating species is contemplated for use in the present invention, Azospirillum and/or Rhizobium will be exemplified in the detailed description set forth herein below, which describes how to make and use the flocculated microbial crop inoculants of the present invention.

I. PREPARATION OF MICROBIAL FLOCS AND CO-FLOCS

In a preferred embodiment, bacteria such as Azospirillum and/or Rhizobium are induced to flocculate by growing them under specific culture conditions. As described above, flocs produced under such conditions are of a macroscopic, rather than microscopic nature, forming large clumps that can be easily separated from the culture medium.

*Azospirillum brasilense* and *Azospirillum lipoferum* are known to grow well in culture media on a variety of carbon sources, and either species may be utilized in the present invention. Various cultured strains of *A. brasilense* and *A. lipoferum* are widely available. *A. brasilense* Sp7 (ATCC Accession No. 29145) and *A. lipoferum* 59b (ATCC Accession No. 29707) may be obtained from the American Type Culture Collection, Rockville, Md. See Sadasivan et al., J. Bact., 163:716–23 (1985). Natural isolates of Azospirillum may also be utilized in the present invention.

Other flocculating bacteria, such as *Rhizobium spp.*, may also be utilized according to the methods described herein for Azospirillum. *Rhizobium leguminosarum bv Phaseoli* (USDA National Rhizobium Culture Collection Strain No. 2743) is one example of a Rhizobium species that grows well in culture and flocculates readily under the specific culture conditions described herein. This and other species of Rhizobium are commonly available.

Cultured Azospirillum or Rhizobium species may be induced to shift to a cyst-forming morphology and to flocculate, by growing the cells under specific culture conditions. A suitable culture medium comprises mineral salts essential for bacterial growth, a carbon source and a nitrogen source. The ratio of carbon to nitrogen in the culture medium is important for the control and induction of flocculation. The carbon to nitrogen ratio should be at least 30:1. In a preferred embodiment, the ratio is at least 50:1, and, most preferably, about 80:1.

A carbon source for the Azospirillum growth medium may be selected from the group including malate, gluconate, α-ketoglutarate, succinate, fructose and glucose. Other carbon sources may also be useful, and these can be determined easily by one skilled in the art. Fructose is preferred for producing Azospirillum-based inoculants in the practice of the present invention because both *A. brasilense* and *A. lipoferum* display excellent flocculent growth when fructose is used as the carbon source. Gluconate induces good floc formation in both species, whereas α-ketoglutarate and glucose induce floc formation of *A. lipoferum* but not of *A. brasilense*. See Sadasivan et al., J. Bact., 163:716–23 (1985). Succinate is preferred for producing inoculants comprising co-flocs of Rhizobium and Azospirillum, since both bacteria flocculate well when succinate is used as the carbon source.

If fructose or succinate is used as the carbon source, it should be provided at a concentration of between 5–100 mM. In a preferred embodiment, 8–10 mM fructose or succinate is used.

Nitrogen sources useful in the growth medium of the present invention include potassium nitrate ($KNO_3$), ammonium nitrate ($NH_4NO_3$) and glutamate. Other nitrogen sources may also be useful. Potassium nitrate is preferred in the practice of the present invention because, when used in conjunction with 8 mM fructose or succinate, it induces excellent flocculent growth of both *A. brasilense* and *A. lipoferum*, as well as *Rhizobium leguminosarum*. Potassium nitrate should be provided at a concentration of between 0.2–1.0 mM. In a preferred embodiment, 0.5 mM $KNO_3$ is used.

Thus, a preferred medium for growth and flocculation of Azospirillum species comprises 8 mM fructose and 0.5 mM $KNO_3$ in minimal medium. Minimal medium is defined herein as a medium comprising mineral salts and, optionally, organic acids and trace amounts of other components, necessary for growth of a particular microorganism. The formulation of minimal media for microbial culture is well known in the art. A preferred minimal medium for culture of Azospirillum species comprises the following ingredients: 0.2 g/l $MgSO_4.7H_2O$; 0.1 g/l NaCl; 0.02 g/l $CaCl_2$; 0.06 g/l Fe(EDTA); 0.02 g/l $Na_2MoO_4.2H_2O$; 0.01 g/l $MnSO_4.H_2O$; 4.9 g/l KOH; 5.0 g/l malic acid; 0.02 g/l yeast extract (Difco); in a 10 mM phosphate buffer, final pH adjusted to 6.8. Variations and substitutions in this type of minimal medium can be made, and will be apparent to those skilled in the art. The preparation of Azospirillum growth medium for producing a flocculent growth pattern is set forth in greater detail in Example 1 below.

A preferred medium for growth and flocculation of Rhizobium species or Azospirillum and Rhizobium species combined comprises 8 mM succinate and 0.5 mM $KNO_3$ in minimal medium, as described above. The preparation of growth medium for Rhizobium or Rhizobium/Azospirillum for producing a flocculent growth pattern is the same as set forth for Azospirillum in Example 1 below.

Liquid cultures of Azospirillum and/or Rhizobium are grown according to standard methods. Inocula are grown in nutrient-rich media and log-phase cultures transferred to the flocculation media described above. Flocculation media are generally inoculated to an optical density of between 0.3 and 1.0. Small culture batches may be incubated at 30°–35° C. on a Gyrotory shaker (New Brunswick Scientific Company, Inc., Edison, N.J.) at 200 rpm for 18–24 hours. For larger batches, cultures may be grown in an aerated fermentor at 30°–35° C. overnight. During the incubation period, the bacteria multiply and flocculate, and can be harvested on the following day.

Azospirillum and/or Rhizobium flocs readily settle to the bottom of a liquid culture, if left to stand. Hence, flocs are easy to harvest, without a necessity for centrifugation. Culture medium is decanted from the flocs, which thereafter may be stored or used as wet flocs, or may be dried, e.g., by air drying. Alternatively, culture medium may be removed from flocculents by coarse filtration methods (i.e., through fine mesh, cloth or porous filter paper), and thereafter used or stored as wet flocs, or dried.

Harvested Azospirillum and/or Rhizobium flocs provide a high density inoculum containing approximately $10^{11}$ cells/gm of wet floc or $10^{12}$ cells/gm of dry floc. Flocculated inoculum may be stored for long periods of time with no appreciable loss of cell viability, as described in greater detail for Azospirillum in Example 1 below.

According to another aspect of the present invention, flocculated bacteria, such as Azospirillum or Rhizobium, or a combination thereof, can be used for the delivery of other microorganisms that confer beneficial properties to plants, such as nitrogen fixation, production of secondary metabolites, production of antibiotics useful in biological control of plant pests and production of plant growth regulators. Other bacteria are preferred for delivery by flocculated bacteria in the present invention; however, other classes of microorganisms (e.g., cyanobacteria or fungi) may also be utilized.

These other agriculturally beneficial microorganisms are prepared for delivery by flocculated Azospirillum and/or Rhizobium, for example, simply by co-culturing the selected microorganism with Azospirillum and/or Rhizobium in appropriate medium, as described above. The cells become entrapped in the flocs, to produce an inoculant comprising the flocculating bacterium and the additional microorganism (sometimes referred to herein as a "co-floc"). Co-flocs of Azospirillum and Rhizobium, produced by co-cultivation and flocculation of the co-cultivated species, are described hereinabove. It should be noted that unless, like Azospirillum and Rhizobium co-flocs, the selected microorganism itself differentiates (i.e., becomes encysted) under the same culture conditions as Azospirillum or Rhizobium, that the additional microorganism may not possess the longevity of encysted Azospirillum or Rhizobium cells. Even so, the polysaccharide matrix comprising the floc confers a certain amount of protection to the other microorganisms, as demonstrated in Example 2 below.

Bacterial flocs containing additional beneficial microorganisms are preferably stored under refrigeration, or frozen, as wet floc, instead of being dried. However, drying may be suitable for some of these additional microorganisms, as can be easily determined empirically by one skilled in the art.

In an alternative embodiment, additional microorganisms may be mixed with Azospirillum, Rhizobium or other flocculating bacteria subsequent to flocculation (sometimes referred to herein as "mixed flocs"). However, in mixed flocs, the additional microorganisms do not become as securely entrapped in the biopolymer matrix of the flocculated bacteria as they do in co-flocs, as shown in Example 2.

Beneficial microorganisms having similar growth rates are preferred for use in the production of co-flocs. Bacteria having slower or faster growth rates may also be utilized, but the initial concentration of cells used to inoculate the liquid culture should be adjusted to take into account the difference in growth rate. Examples of bacterial species that may be successfully co-flocculated with Azospirillum and/or Rhizobium, for example, include *Bacillus spp.* and *Enterobacter spp.*, certain of which have antifungal or insecticidal properties, and *Pseudomonas spp.*, certain species of which (e.g., *P. putida*) enhance nodulation in leguminous plants and other species of which (e.g., *P. gladioli*) possess antifungal activity. Examples of the preparation and use of co-flocs and mixed flocs of Azospirillum comprising these microorganisms are set forth in Example 2 below.

II. USE OF FLOCCULATED MICROBIAL INOCULANTS TO IMPROVE CROP PRODUCTIVITY

Application of flocculated microbial inoculants for agricultural purposes includes several simple techniques, such as coating seeds with the inoculant, mixing the inoculant into soil or germination media and spraying the inoculant onto various portions of plants. Such methods are familiar to agronomists and do not call for sophistication in processing and equipment. Because of the simplicity of the procedures involved, use of flocculated microbial inoculant is cost-effective. Furthermore, because of the adhesive nature of the flocs, there should be no need for the use of additional carriers or adhesive materials. Also, since the floc material is a biopolymer, it is easily degradable in soil and should not present an environmental hazard.

Seeds may be coated with flocculated microbial inoculants simply by mixing wet flocs with dry seeds or alternatively, dry flocs with wet seeds during seed priming, to aid in the attachment of flocs to seeds surfaces. For example, 10 ml of flocculated Azospirillum contains approximately $10^{11}$ cells. The floc may be air dried or kept moist. This amount of floc, when combined with one pound of seed (e.g., grass seed) results in a seed coating of approximately $10^5$–$10^6$ cells/seed. Such coating is sufficient to impart the beneficial effect of the bacteria, as discussed in greater detail in Example 3 below. The amount of inoculant to be applied to other types of seeds may be easily determined by one skilled in the art. Survival of flocculated Azospirillum on grass seed is described more fully in Example 3 below.

Flocculated Azospirillum inoculant is particularly useful for coating various grass seeds, since these organisms are found naturally in association with grasses, including economically important turf grasses, as well as agronomically important cereal crops, such as corn. See Lamm et al., Can. J. Microbiol., 27: 1320–25 (1981). Similarly, flocculated Rhizobium inoculant is particularly useful for coating seeds of leguminous plants, since various rhizobia are symbionts with roots of legumes, forming root nodules in which the bacteria fix atmospheric nitrogen. It has been discovered in accordance with the present invention that inoculants of flocculated Rhizobium enhance the nodulation process as compared to non-flocculated Rhizobium inoculants. Moreover, co-flocs of Rhizobium and Azospirillum have been found to even further enhance nodulation of leguminous roots. These observations are described in detail in Example 6 below.

Bacterial co-flocs containing other beneficial microorganisms are useful for a wide variety of seeds, including vegetable seeds, such as tomato, pepper, radish and eggplant. In accordance with the present invention, Azospirillum flocs have been found to adhere well to such vegetable seeds.

Flocculated microbial inoculants may also be used to inoculate planting media, such as soil, potting mixtures, or other germination mixtures prior to planting seeds. This is accomplished simply by mixing flocs (preferably dry) with planting mixtures (at a rate of, e.g., approximately $10^6$ cells/gm). Dry flocs can be mixed with dry planting mixtures and stored for extended periods of time before use. Survival of Azospirillum flocs in soil and other germination mixtures is described more fully in Example 4 below.

In a preferred embodiment of the present invention, flocculated microbial inoculants are utilized to advantage in seed priming, a method of controlled hydration in which germination is initiated at a proper temperature, oxygen and water potential. Seed priming is a pre-sowing treatment developed to improve seedling emergence and establishment. The treatment involves placing seeds in an osmotic medium of pre-determined water potential. Under these conditions, seeds are able to imbibe water and complete early phases of germination, under sufficient water stress to prevent the completion of germination (i.e., emergence of the radicle).

In the practice of the present invention, a preferred method of priming seeds is through the use of a solid matrix system based on controlling water availability to the germinating seeds by matrix potential. Seeds are primed using a specific amount of water, solid matrix and seeds, such as that disclosed in U.S. Pat. No. 4,912,874 (Apr. 3, 1990). For example, a combination of vermiculite and polyethylene glycol has been utilized for osmoconditioning seeds. Vermiculite and water in a closed container has also been utilized. These solid matrices may be dried and mixed with dry flocculated microbial inoculum and stored for future use. Alternatively, mixtures of seed priming matrix and inoculant may be combined moist and stored under refrigeration or used immediately. Under either circumstance, flocculated microorganisms, such as Azospirillum and/or Rhizobium, provide an ideal inoculant for seed priming systems utilizing solid matrices.

Bacterial flocs and co-flocs may also be mixed with field soil prior to planting for improving crop productivity. This may be accomplished by spreading and mixing floc along with fertilizers or other pre-planting soil treatment. Such methods are well known to agronomists.

Flocculated microbial inoculants may also be applied to selected portions of plants to improve crop productivity. As one example, wet or dry flocs may be sprayed on the lower leaf portions of turfgrass sod patches to promote root growth. As another example, co-flocs comprising bacteria that produce antifungal or insecticidal compounds (e.g., *Bacillus spp., Pseudomonas spp.*) may be sprayed on plant leaves and stems as a biological control of such pests and pathogens. Alternatively, they may be applied as a seed coating to protect the newly-emerging root.

The present invention provides for the application of flocculated forms of microorganisms as a source of crop inoculant and delivery system for other agronomically beneficial microorganisms. Flocculated microbial inoculants possess enhanced survivability on dry surfaces such as seeds of turf, forage and grain grasses for prolonged storage. The process is likewise useful for use with vegetable seeds, and is compatible with mixing various soil and germination media. The microenvironment of flocculated microorganisms is highly protective against physical and chemical stresses and provides a safe niche for survival and cell release upon seed sowing in favorable surroundings.

Flocculated microbial inoculants are prepared and applied according to simple, inexpensive techniques. Hence, microbial flocs, either alone or in combination with other beneficial microorganisms, provide a superior method of delivering agronomically useful microbes for increased crop productivity.

The following examples are provided to describe the invention in further detail. These examples are intended merely to illustrate and not to limit the invention.

EXAMPLE 1

Preparation and Survival Characteristics of Flocculated Azospirillum

Flocculation of *Azospirillum brasilense* Sp7 (ATCC 29145) and *Azospirillum lipoferum* Sp59b (ATCC 29707) was accomplished according to the following method. A liquid growth medium (sometimes referred to herein as "flocculation medium"), containing minimal salts medium, 8 mM fructose and 0.5 mM $KNO_3$, was prepared. The minimal salts medium contained the following ingredients: 0.2 g/l $MgSO_4.7H_2O$; 0.1 g/l NaCl; 0.02 g/l $CaCl_2$; 0.06 g/l Fe(EDTA); 0.02 g/l $Na_2MoO_4.2H_2O$; 0.01 g/l $MnSO_4.H_2O$; 4.9 g/l KOH; 5.0 g/l malic acid; 0.02 g/l yeast extract (Difco); in a 10 mM phosphate buffer, final pH adjusted to 6.8. Salts other than organic carbon, inorganic nitrogen, or phosphate salts for 1 liter of medium were dissolved in 10 ml of distilled water and autoclaved separately. After cooling, the salts were added to 940 ml of sterile phosphate buffer (10 mM, pH 6.8). Iron salt was filter sterilized before being added to the minimal salts medium. Malic acid, fructose and $KNO_3$ were filter sterilized and added individually to the medium. The final volume of the liquid growth medium was made 1 liter.

Inocula of *A. brasilense* or *A. lipoferum* were harvested from log-phase cultures grown in nutrient broth (NB; Difco; comprising Typtone and Beef extract and having a low C:N ratio) by centrifugation at 3,000×g for 10 minutes at 4° C. Pellets were washed three times with equal volumes of 0.01M phosphate buffer (pH 6.8) and inoculated into the flocculation growth medium to an initial optical density at 660 nm of 0.3 to 0.4. Cultures were grown in 250 ml flask containing 100 ml of medium. The cultures were incubated at 34° C. on a Gyrotory shaker (New Brunswick Scientific Company, Inc., Edison, N.J.) at 200 rpm and harvested after overnight incubation. Alternatively, cultures were grown in large batches with 5-liter bottles containing 4 liters of media. The large batch cultures were incubated with vigorous air sparging at 34° C. overnight.

Flocculated Azospirillum cells were harvested by decanting the culture fluid from the flocculated cells. A 100 ml culture of flocculation medium yielded approximately 20 ml of wet floc. To determine the stability of wet floc versus dry flocculent, a 20 ml harvest of wet floc was divided into two 10 ml batches. One batch was maintained as a wet floc, while the other batch was air-dried to a powder. Each batch contained approximately $10^{11}$ Azospirillum cells.

Survival of *Azospirillum brasilense* as wet floc or as dry floc was analyzed according to the following procedure. Wet flocs were stored at 4° C., and aliquots were periodically removed for viability measurements. Dry flocs were stored at room temperature, and aliquots were periodically removed for viability measurements. Viability of the wet or dry flocs was determined by incubating approximately 0.1 ml of wet floc, or approximately 10 mg dry floc in 100 ml phosphate buffer for 27–28 hours at room temperature. 0.1 ml of the incubated floc was then plated for viable counts on semi-selective nutrient agar (NB containing 1.5% agar and 15 µg/ml streptomycin) and incubated at 42° C., according to standard methods. Viability was determined by measuring the number of colony-forming units (cfu) per 0.1 ml wet floc or per 10 mg dry floc.

Table 1 shows the survival of *Azospirillum brasilense* as a wet flocculent or dry flocculent for 60 days following harvesting.

TABLE 1

Survival of Flocculated Azospirillum

| Time (Days) | Viability | |
|---|---|---|
| | Wet Flocculent (log cfu/0.1 ml) | Dried Flocculent (log cfu/10 mg) |
| 0 | 7.202 | 7.529 |
| 15 | 7.002 | 6.946 |
| 30 | 7.151 | 7.394 |
| 45 | 7.290 | 7.183 |
| 60 | 7.339 | 7.204 |

As can be seen from Table 1, no appreciable decrease in cell viability was observed for the entire 60 day period, regardless of whether the Azospirillum was stored at 4° C. as a wet floc or at room temperature as a dry floc.

In an extended observation, survival of *Azospirillum brasilense* as a dry floc was measured up to 6 months from the time of harvesting. No appreciable loss of cell viability was observed in dry flocs of Azospirillum over the 6 month period. Wet flocs were observed for cell viability up to 90 days, at which time no appreciable loss of viability was observed.

EXAMPLE 2

Co-Flocculation of *Enterobacter cloacae* and *Pseudomonas putida* with *Azospirillum brasilense*

The following procedures were performed to demonstrate the enhanced entrapment and survival of beneficial rhizobacteria in flocculated Azospirillum. Co-flocs of Enterobacter or Pseudomonas and Azospirillum were formed by inoculating rifampicin-resistant strains of Enterobacter or Pseudomonas in flocculation growth medium just prior to floc formation by Azospirillum (6 hours after Azospirillum inoculation) and incubated 12 additional hours under the conditions described in Example 1. As a control, a "mixed flocculent" was formed by mixing cells of Enterobacter and Pseudomonas with previously-flocculated *A. brasilense* (prepared according to the method set forth in Example 1) in phosphate buffer.

To determine the degree of entrapment of Enterobacter or Pseudomonas in mixed flocs versus co-flocs, mixed flocs or co-flocs (0.1 ml respectively) were mixed with 1 ml buffer and vortexed for 30 seconds at full speed. Mixed flocs and co-flocs were washed an additional 2 times with 1 ml of buffer, followed by vortexing at 30 seconds at full speed. Following each wash, an aliquot of the each floc was incubated in buffer for 27-28 hours, as described in Example 1. Viable counts of Enterobacter and Pseudomonas in mixed- or co-flocs were then determined by plating on nutrient agar with rifampicin (100 µg/ml) and measuring colony-forming units, as described in Example 1. Table 2 shows the results of the above-described procedure.

TABLE 2

Effect of Co-flocculation vs. Mixed Flocculation on Release of *Enterobacter cloacae* and *Pseudomonas putida* from Azospirillum Flocs

| | Viability (log cfu/ml wet flocculent) | | | |
|---|---|---|---|---|
| | Enterobacter | | Pseudomonas | |
| Wash | Mixed Floc | Co-floc | Mixed Floc | Co-floc |
| 1 | 7.000 | 10.450 | 7.450 | 10.000 |
| 2 | 5.510 | 10.340 | 7.190 | 10.000 |
| 3 | 5.450 | 9.000 | 6.950 | 10.000 |

As can be seen from Table 2, both Enterobacter and Pseudomonas were better retained in Azospirillum flocs if they had been co-inoculated with growing Azospirillum just prior to flocculation (i.e., co-flocculated), than if they had been mixed with Azospirillum floc subsequent to flocculation. This is likely due to the fact that biopolymer matrix formation more securely entraps co-cultured Enterobacter and Pseudomonas when they are present during the actual formation of biopolymer, than when they are added to the polymer matrix later.

The survival of Enterobacter and Pseudomonas in Azospirillum flocs was also examined. Co-flocs of *Azospirillum brasilense*, *Enterobacter cloacae* or *Pseudomonas putida* were prepared as described above. Flocs were harvested as described in Example 1, and stored as wet floc at 4° C. for up to 4 months. Results are shown in Table 3.

TABLE 3

Survival of *Enterobacter cloacae* and *Pseudomonas putida* in Flocculated Azospirillum

| Time | log cfu/ml wet flocculent | |
|---|---|---|
| (Months) | Enterobacter | Pseudomonas |
| 0 | 10.450 | 10.000 |
| 1 | 9.400 | 9.750 |
| 2 | 8.250 | 8.700 |
| 4 | 5.900 | 7.950 |

As shown in Table 3, both Enterobacter and Pseudomonas showed good survival rates as co-flocs of Azospirillum, when stored at 4° C. for 1, 2 or 4 months. Between $10^9$ and $10^{10}$ viable colony-forming-units of both Enterobacter and Pseudomonas per ml wet floc were present after one month of storage at 4° C. After 4 months of storage, approximately $10^6$ cfu/ml viable Enterobacter was present per ml wet floc, while approximately $10^8$ colony-forming-units per ml wet floc of Pseudomonas was present. In comparison, viable counts of non-flocculated Pseudomonas or Enterbacter have been observed to fall to less than $10^4$ cfu/ml within one month. These data indicate that flocculated Azospirillum provides a protective storage medium for other beneficial rhizobacteria to be later inoculated onto seeds, plants or soil.

EXAMPLE 3

Comparison of Survival of Flocculated and Non-Flocculated Azospirillum on Three Varieties of Turf Grass The survival of non-flocculated versus flocculated *Azospirillum brasilense* on turf grass seeds was compared. Initial inoculum of either non-flocculated or flocculated cells was applied in 1 ml buffer at a level of $10^8$ cfu/g seed, and dried under air flow. At intervals between 0 and 60 days after treatment, a pre-determined amount of seed was tested for the presence of viable Azospirillum by washing the seeds in an aliquot of buffer and plating equivalent amounts of buffer on nutrient agar, as described in Example 1. Seeds of Kentucky bluegrass, perennial ryegrass and tall fescue grass were treated in this manner. Results are shown in Table 4.

TABLE 4

Viability of Flocculated Vs. Nonflocculated Azospirillum in Seed Coatings of Three Turf Grasses

| Time | Viability (log cfu/q seed) | | | | | |
|---|---|---|---|---|---|---|
| | Kentucky Bluegrass | | Perennial Ryegrass | | Tall Fescue | |
| (Days) | Floc | Non-floc | Floc | Non-floc | Floc | Non-floc |
| 0 | 7.688 | 7.544 | 7.830 | 7.820 | 7.672 | 7.469 |
| 15 | 7.845 | 6.440 | 7.840 | 6.690 | 7.929 | 5.900 |
| 30 | 7.648 | 4.707 | 7.602 | 5.204 | 7.894 | 5.767 |
| 45 | 7.505 | 3.685 | 7.270 | 5.164 | 7.788 | 4.531 |
| 60 | 7.694 | 3.544 | 7.607 | 4.620 | 7.790 | 3.662 |

As shown in Table 4, flocculated Azospirillum demonstrated superior survivability on all three varieties of grass, as compared with non-flocculated Azospirillum inoculant. The number of viable cells per gram of seed remained relatively constant for 60 days on all three varieties of turf grass, when flocculated cells were utilized as the inoculant. In contrast, a significant decline in viable cell number per gram seed was observed on all three turf grass varieties over the course of 60 days, when non-flocculated Azospirillum was used as the inoculant. These results demonstrate the superior survivability of flocculated Azospirillum as an inoculant for seed coating.

Survival of flocculated and non-flocculated *Azospirillum brasilense* on turfgrass seeds at room temperature was also observed by measuring the percent of seeds yielding Azospirillum over the course of 24 weeks. These results are shown in Table 5.

TABLE 5

Turfgrass Seeds Yielding Flocculated vs. Non-Flocculated Azospirillum Inoculant Applied as Seed Coating

| Time | % Seeds Yielding Azospirillum | | | | | |
|---|---|---|---|---|---|---|
| | Kentucky Bluegrass | | Perennial Ryegrass | | Tall Fescue | |
| (Weeks) | Floc | Non-floc | Floc | Non-floc | Floc | Non-floc |
| 0 | 100 | 100 | 100 | 100 | 100 | 100 |
| 1 | 98 | 93 | 100 | 99 | 100 | 98 |
| 2 | 100 | 96 | 99 | 97 | 100 | 95 |
| 3 | 98 | 82 | 99 | 83 | 98 | 83 |
| 4 | 98 | 79 | 98 | 76 | 95 | 77 |
| 8 | 90 | 58 | 84 | 61 | 83 | 70 |
| 16 | 76 | 33 | 74 | 32 | 76 | 40 |
| 24 | 41 | 14 | 70 | 23 | 69 | 12 |

As can be seen from Table 5, Azospirillum inoculant applied as a floc could be isolated from 95-100% of seeds from each turfgrass variety for the first four weeks after treatment. Thereafter, the percent of seeds yielding Azospirillum fell off to a final percentage of 41% (Kentucky bluegrass)—70% (perennial ryegrass and tall fescue) after 24 weeks of storage at room temperature. In contrast, Azospirillum inoculant applied in a non-flocculated form began to show decline in survival rate after the first week or two. The percent of seeds yielding non-flocculated Azospirillum decreased steadily over the 24-week period, reaching a final percentage of 12% (tall fescue)—23% (perennial ryegrass). These results again show the superior survivability of flocculated Azospirillum inoculant.

Upon germination, seeds coated with flocculated Azospirillum developed roots that were colonized with the Azospirillum cells. Additionally, tall fescue seeds inoculated with a seed coating of flocculated Azospirillum demonstrated a superior growth rate, as compared with non-inoculated seeds.

EXAMPLE 4

Survival of Flocculated Azospirillum Inoculants in Soil and Other Germinating Mixtures Survival of flocculated Azospirillum in soil was demonstrated according to the following procedure. Wet Azospirillum floc was mixed with soil at a rate of 0.5 or 1.0 ml of floc per gram. The inoculated soil was then dried and stored at room temperature for up to four months.

As shown in Table 6, the survival of flocculated Azospirillum in soil remained virtually unchanged during four months of storage at room temperature. Thus, flocculated Azospirillum provides a stable inoculant for soil.

TABLE 6

Survival of Floccuated Azospirillum in Soil

| Time | Viability (log cfu/g soil) | |
|---|---|---|
| (Months) | 0.5 ml Floc | 1.0 ml Floc |
| 0 | 7.475 | 8.232 |
| 1 | 7.869 | 8.247 |
| 2 | 7.481 | 8.369 |
| 3 | 7.416 | 8.303 |
| 4 | 7.519 | 8.387 |

The release from wet floc and growth of *Azospirillum brasilense* was also observed in a soil priming mixture at three different temperatures, over a period of five days. The soil priming mixture comprised approximately equal volumes of calcined clay (neutral), water and tall fescue seed. The soil priming mixture was inoculated at an approximate density of $10^6$ cfu/g of mixture. Results are shown in Table 7.

TABLE 7

Release from Wet Floc and Growth of Azospirillum in a Soil Priming Mixture

| Time | Viability (log cfu/g mixture) | | |
|---|---|---|---|
| (Days) | 4° C. | 20° C. | 30° C. |
| 0 | 6.010 | 5.948 | 6.009 |
| 2 | 6.222 | 7.073 | 7.963 |
| 3 | 5.395 | 6.827 | 8.026 |
| 4 | 5.426 | 7.165 | 8.223 |
| 5 | 5.365 | 7.184 | 8.185 |

As can be seen in Table 7, when the mixture was incubated at 4° C. for five days, the Azospirillum remained at that number for the first two days, then declined somewhat over the following three days. Upon incubation at 20° C., Azospirillum cells multiplied from $10^6$ to $10^7$ cfu/g soil priming mixture, and remained at that level. When incubated at 30° C., Azospirillum cells multiplied from $10^6$ to about $10^8$ cfu/g soil priming mixture in the first two days, and remained at that level for the subsequent three days. Thus, the cell release and growth of flocculated Azospirillum in a soil priming mixture can be regulated by storage and/or incubation at selected temperatures.

EXAMPLE 5

Preparation of Flocculated Rhizobium and of Rhizobium/Azospirillum Co-flocs

Flocculation of *Rhizobium leguminosarum* bv *Phaseoli* was accomplished according to the methods set forth in Example 1, with the following modifications. Initial inoculum *Rhizobium leguminosarum* bv *Phaseoli* (USDA National Rhizobium Culture Collection Strain No. 2743, available from U.S. Department of Agriculture Research Center, Beltsville, Md. 20745) was grown in a submerged culture containing 4 g/L of Nutrient Broth (Difco), 5 g/L mannitol, 0.5 g/L Yeast Extract (Difco) and mineral salts. The culture was initiated with Rhizobium cells adjusted to an initial optical density of about 0.2. Cultures were grown in a temperature controlled water bath under continuous shaking (150 revolutions/min). Log-phase cells were harvested by centrifugation and the pellet transferred to a flocculation medium as described in Example 1, but containing 8 mM succinic acid instead of fructose.

For production of co-flocs of Rhizobium and Azospirillum, an initial inoculum of *Azospirillum brasilense* strain Cd and *Rhizobium leguminosarum* bv *Phaseoli* were grown, as described above. Cultures were initiated with a 1:1 mixture containing both Azospirillum and Rhizobium cells adjusted to an initial optical density of about 0.2. The cultures were harvested and transferred to succinic acid-containing flocculation medium as described above.

Table 8 shows a typical growth curve from co-cultivation of Rhizobium and Azospirillum in Nutrient Broth/Yeast Extract culture medium.

TABLE 8

Rhizobium/Azospirillum Growth Curve

| Time (h) | Optical Density (600 nm) |
|---|---|
| 0 | 0.200 |
| 2 | 0.210 |
| 4 | 0.490 |
| 6 | 0.740 |
| 8 | 1.210 |
| 10 | 1.460 |
| 12 | 1.530 |
| 14 | 1.570 |

As can be seen from Table 8, co-cultivated Rhizobium and Azospirillum exhibited a typical growth curve, as demonstrated by the change in optical density at 600 nm for the overnight period. A similar growth curve was obtained when *Rhizobium leguminosarum* was cultivated singly.

To demonstrate the ability of Rhizobium (alone or together with Azospirillum) to flocculate extensively, log-phase Rhizobium or Rhizobium/Azospirillum cultures grown in the NB/Yeast Extract medium described above were harvested, washed and inoculated into flocculation medium at an initial optical density of 1.000. Cultures were incubated in the flocculation medium for several hours, as described in Example 1 above. Aliquots were removed at intervals during the flocculation time period for measurement of optical density. Flocculation of Rhizobium or Rhizobium/Azospirillum was observed as decrease in optical density of the culture over the incubation time period.

Table 9 shows the flocculation of *Rhizobium leguminosarum* over a 14-hour incubation time.

TABLE 9

Flocculation of *Rhizobium Leguminosarum* by *Phaseoli* in Flocculation Medium Containing 8 mM Succinate

| Time (h) | Optical Density (600 nm) |
|---|---|
| 0 | 1.000 |
| 2 | 0.940 |
| 4 | 0.900 |
| 6 | 0.489 |
| 8 | 0.320 |
| 10 | 0.300 |
| 12 | 0.296 |
| 14 | 0.210 |

Table 10 shows the flocculation of co-cultivatived Rhizobium and Azospirillum.

TABLE 10

Co-Flocculation of Rhizobium and Azospirillum in Flocculation Medium Containing 8 mM Succinate

| Time (h) | Optical Density (600 nm) |
|---|---|
| 0 | 1.000 |
| 2 | 1.000 |
| 4 | 0.920 |
| 6 | 0.489 |
| 8 | 0.320 |
| 10 | 0.300 |
| 12 | 0.297 |
| 14 | 0.211 |
| 16 | 0.211 |

As can be seen from Tables 9 and 10, extensive flocculation of Rhizobium or Rhizobium/Azospirillum cultures can be obtained by transferring the bacteria to the appropriate flocculation medium. Incubation of the cultures in the flocculation medium results in formation of large aggregates of Rhizobium or Rhizobium/Azospirillum flocculents, which settle to the bottom of the culture medium container, and can be easily separated from the culture medium, as described hereinabove for Azospirillum.

EXAMPLE 6

Nodulation Efficiency of *Rhizobium Leguminosarum* bv *Phaseoli*: Comparison of Flocculated Versus Non-Flocculated Rhizobium and Effect of Adding Azospirillum The effect of flocculation on the ability of *Rhizobium leguminosarum* to stimulate nodule formation was measured. Additionally, the effect of added Azospirillum (either in flocculated or non-flocculated form) was also measured. *Rhizobium leguminosarum* bv *Phaseoli*, either singularly or in conjunction with *Azospirillum brasilense* strain Cd, was grown through log phase culture in Nutrient Broth/Yeast Extract medium, as described in Example 5 above. For testing of non-flocculated bacteria, these cultures were harvested and used without further treatment. For testing of flocculated bacteria, log phase cultures were pelleted, washed and incubated in flocculation medium, as described in Example 5 above. Inocula comprising equivalent numbers of cells were utilized for each of four treatments. All inocula were applied as seed coating to *Phaseolus vulgaris* L. [Navy Bean], prior to planting the seeds. Twenty days after planting, plants were uprooted and the number of nodules per plant was counted (8 pots per treatment, one plant per pot). Results of this study are shown in Table 11.

TABLE 11

Effect of Flocculated Versus Non-Flocculated Form and Addition of Azospirillum on the Nodulation Efficiency of *Rhizobium leguminosarum* by Phaseoli

|  | All Bacteria Non-Flocculated | All Bacteria Flocculated |
|---|---|---|
| Rhizobium only | 93.25 ± 8.24 | 188.75 ± 2.75 |
| Rhizobium and Azospirillum | 170.00 ± 39.31 | 216.25 ± 3.30 |

As can be seen from Table 11, the use of flocculated Rhizobium versus non-flocculated Rhizobium as a seed coating resulted in a doubling of the number of root nodules per plant twenty days after planting. This result confirms the superiority of flocculated Rhizobium as an inoculum for promoting root nodulation in legumes.

Notably, the addition of non-flocculated Azospirillum to non-flocculated Rhizobium also resulted in a dramatic increase in nodulation, which approached the nodulation frequency obtained from inoculation with flocculated Rhizobium. The highest nodulation efficiency was observed, however, when co-flocs of Rhizobium and Azospirillum were used to inoculate seeds. Using the co-floc inoculant, nodulation frequency was increased approximately 2.3-fold over that obtained by seed coating with non-flocculated Rhizobium only, approximately 1.27-fold more than that observed when non-flocculated Rhizobium and Azospirillum were used, and approximately 1.15-fold greater than when flocculated Rhizobium only was used. These results indicate that, for maximum nodulation efficiency, an inoculent comprising co-flocs of Rhizobium and Azospirillum gives superior results.

While certain preferred embodiments of the present invention have been illustrated and described, the present invention is not limited to these embodiments. For example, flocculated bacterial inoculants may also be applied in the area of environmental science and engineering. Co-flocs comprising, e.g., Azospirillum and environmentally active microorganisms (e.g., pollutant-degrading bacteria) may be introduced into contaminated soils or other subsurface environments to degrade specific contaminants. Flocculated Azospirillum comprising such bacteria can provide a protective environment, enabling the detoxifying bacteria to survive longer under field conditions. One example of an environmentally-useful bacterium having potential utility as a co-floc is *Flavobacterium sp.*, which is a gram-negative aerobic bacterium that degrades a variety of chlorinated phenols. See Stormo et al., App. Env. Microbiol., 58:727–30 (1992).

What is claimed is:

1. A method of delivering microorganisms to a plant to improve plant productivity, which comprises inoculating a plant component under agronomical conditions with a preformed co-floc comprising a combination of *Azospirillum spp.* and *Rhizobium spp.*, said plant component being selected from the group consisting of seeds, stems, roots, flowers and leaves.

2. A method of preparing a mixture comprising a seed and microbial inoculant mixture for beneficial augmentation of plant growth, said inoculant including a co-flocculent of *Azospirillum spp.* and *Rhizobium spp.*, said method comprising the steps of:
   a) providing a flocculation medium comprising mineral salts and organic acids necessary for growth of said *Azospirillum spp.* and *Rhizobium spp.*, a carbon source and a nitrogen source, the ratio of carbon to nitrogen in said flocculation medium being at least 30:1;
   b) culturing said *Azospirillum spp.* and *Rhizobium spp.* in said flocculation medium under conditions promoting growth and flocculation of said *Azospirillum spp.* and *Rhizobium spp.*, thereby producing a co-floc comprising *Azospirillum spp.* and *Rhizobium spp.*;
   c) harvesting said co-floc: and
   d) mixing said co-floc with said seed, thereby producing a mixture of seed and microbial inoculant comprising a flocculated form of said *Azospirillum spp.* and *Rhizobium spp.*

3. A method as claimed in claim 1, wherein inoculation is effectuated by admixture of said co-floc with seeds.

4. A method as claimed in claim 1, wherein inoculation is effectuated by spraying said co-floc on said plant components.

5. A method as claimed in claim 1, wherein inoculation is effectuated by admixture of said co-floc with germination media.

6. A method as claimed in claim 1, wherein inoculation is effectuated by admixture of said co-floc with soil.

7. A microbial inoculant for a plant, which comprises a co-floc comprising a combination of *Azospirillum spp.* and *Rhizobium spp.*

8. A microbial inoculant as claimed in claim 7, further comprising at least one additional agriculturally beneficial microorganism selected from the group consisting of *Enterobacter spp.*, *Bacillus spp.*, and *Pseudomonas spp.*

9. A microbial inoculant for a plant which comprises *Azospirillum spp.* coflocculated with an additional microorganism selected from the group consisting of *Enterobacter spp.*, *Pseudomonas spp.*, and *Bacillus spp.*

10. A microbial inoculant for a plant which comprises *Rhizobium spp.* co-flocculated with an additional microorganism selected from the group consisting of *Enterobacter spp.*, *Pseudomonas spp.*, and *Bacillus spp.*

11. A method of preparing a co-flocculated microbial inoculant for a plant, the microorganism constituents of said inoculant comprising a co-floc of *Azospirillum spp.* and *Rhizobium spp.*, said method comprising the steps of:
   a) providing a flocculation medium comprising mineral salts and organic acids necessary for growth of said flocculating microorganisms, and a carbon source and a nitrogen source, the ratio of carbon to nitrogen in said flocculation medium being at least 30:1;
   b) culturing said flocculating microorganisms in said flocculation medium under conditions promoting growth and flocculation of said microorganisms thereby producing a co-floc comprising said microorganisms; and
   c) harvesting said co-floc, thereby producing a microbial inoculant comprising a flocculated form of said microorganisms.

12. A method as claimed in claim 11, wherein said flocculated *Azospirillum spp.* are selected from the group consisting of *A. brasilense* and *A. lipoferum*.

13. A method according to claim 11 wherein said co-floc further comprises an agriculturally beneficial microorganism selected from the group consisting of *Enterobacter spp.*, *Bacillus spp.*, and *Pseudomonas spp.*

14. A method as claimed in claim 11, wherein said flocculated *Rhizobium spp.* is *R. leguminosarum biovar phaseoli*.

15. A method as claimed in claim 2, said method further comprising including in said flocculation medium at least one microorganism selected from the group consisting of *Enterobacter spp.*, *Pseudomonas spp.* and *Bacillus spp.*

16. A method as claimed in claim 2, said method further comprising adding at least one microorganism selected from the group consisting of *Enterobacter spp.*, *Pseudomonas spp.* and *Bacillus spp.* to said co-floc, thereby forming a mixed floc.

* * * * *